US012773687B2

(12) United States Patent
Grasset et al.

(10) Patent No.: US 12,773,687 B2
(45) Date of Patent: Oct. 27, 2026

(54) HYDROFORMYLATION CATALYST SYSTEM WITH SYNGAS SURROGATE

(71) Applicant: V. Mane Fils, Le bar-sur-Loup (FR)

(72) Inventors: Fabien Grasset, Grasse (FR); Piotr Jaunky, Chateauneuf (FR)

(73) Assignee: V. MANE FILS, Le Bar-sur-Loup (FR)

(*) Notice: Subject to any disclaimer, the term of this patent is extended or adjusted under 35 U.S.C. 154(b) by 964 days.

(21) Appl. No.: 17/914,797

(22) PCT Filed: Mar. 26, 2021

(86) PCT No.: PCT/EP2021/058040
§ 371 (c)(1),
(2) Date: Sep. 27, 2022

(87) PCT Pub. No.: WO2021/198113
PCT Pub. Date: Oct. 7, 2021

(65) Prior Publication Data

US 2023/0123090 A1 Apr. 20, 2023

(30) Foreign Application Priority Data

Apr. 1, 2020 (EP) .................................... 20315098

(51) Int. Cl.

| | |
|---|---|
| ***B01J 31/24*** | (2006.01) |
| ***B01J 31/22*** | (2006.01) |
| ***B01J 31/40*** | (2006.01) |
| ***C07C 69/716*** | (2006.01) |

(52) U.S. Cl.
CPC ........... *B01J 31/24* (2013.01); *B01J 31/2217* (2013.01); *B01J 31/4046* (2013.01); *C07C 69/716* (2013.01)

(58) Field of Classification Search
None
See application file for complete search history.

(56) References Cited

U.S. PATENT DOCUMENTS

| | | | | |
|---|---|---|---|---|
| 3,527,809 | A * | 9/1970 | Pruett | C07C 45/50 560/266 |
| 4,021,463 | A | 5/1977 | Kummer et al. | |
| 4,297,239 | A | 10/1981 | Bryant et al. | |
| 7,663,002 | B2 | 2/2010 | Peng et al. | |
| 8,053,605 | B2 | 11/2011 | Choi et al. | |
| 8,426,651 | B2 | 4/2013 | Choi et al. | |
| 9,227,925 | B2 | 1/2016 | Kuma et al. | |
| 10,300,472 | B2 | 5/2019 | Choi et al. | |
| 2008/0033068 | A1 | 2/2008 | Van Leeuwen et al. | |
| 2012/0059195 | A1 | 3/2012 | Choi et al. | |
| 2016/0256862 | A1 | 9/2016 | Eom et al. | |

FOREIGN PATENT DOCUMENTS

| | | |
|---|---|---|
| JP | 2009173611 | 8/2009 |

OTHER PUBLICATIONS

Ren et al ("An Effective Pd-Catalyzed Regioselective Hydroformylation of Olefins with Formic Acid", Journal of the American Society , vol. 138, No. 45 (2016), pp. 14864-11867 (Year: 2016).*

Xian-Dong et al ("Rhodium(I)-catalyzed Pauson-Khand-type reaction using formic acid as a CO surrogate: an alternative approach for indirect CO2 utilization", Green Chemistry, vol. 21, No. 3, (2019), pp. 509-514 (Year: 2019).*

International Search Report dated Jun. 14, 2021 in International Application No. PCT/EP2021/058040.

Written Opinion dated Jun. 14, 2021 in International Application No. PCT/EP2021/058040.

European Search Report dated Aug. 7, 2020 in EP 20 31 5098.

Morimoto, et al.; "Evolution of Carbonylation Catalysis: No Need for Carbon Monoxide.", Angew. Chem. Int. Ed., 2004, 43, 5580-5588.

Wu, et al.: "Carbonylations of Alkenes with CO Surrogates." Angew. Chem. Int. Ed, 2014, vol. 53, pp. 2-13.

Krimen "Acetic Formic Anhdride." Organic Syntheses, Coll. vol. 6 (1988), p. 8; vol. 50, p. 1 (1970).

Franke, et al.: "Applied Formylation." Chem. Rev. (Aug. 31, 2012), vol. 112, pp. 5675-5732.

Leighton, et al.: "Highly Diastereoselective Rhodium-Catalyzed Hydroformylation of Enol Ethers: A Carbonylation-Based Approach to Catalytic Aldol Synthesis." J. Am. Chem. Soc. (1997), vol. 119, pp. 11118-11119.

Wenlong, et al: "An Effective Pd-Catalyzed Regioselective Hydroformylation of Olefins with Formic Acid", Journal of the American Society, vol. 138, No. 45, (Nov. 16, 2016), pp. 14864-14867.

Xian-Dong, et al: "Rhodium(1)-catalyzed Pauson-Khand-type reaction using formic acid as a CO surrogate: an alternative approach for indirect CO2 utilization", Green Chemistry, vol. 21, No. 3, (Jan. 1, 2019), pp. 509-514.

El Ali, et al.: "A Novel Rh—PCy3—CO—COOH Catalytic System for the Regioselective Conversion of Alkenes to Aldehydes." Journal of Molecular Catalysis A: Chemical, vol. 112 (Mar. 4, 1996), pp. 195-201.

(Continued)

*Primary Examiner* — Michael Forrest
(74) *Attorney, Agent, or Firm* — B. Aaron Schulman, Esq.; Stites & Harbison, PLLC

(57) ABSTRACT

Described herein is a hydroformylation catalyst system and method useful for producing aldehydes from olefin substrates, without using carbon monoxide gas. The hydroformylation catalyst system includes a hydroformylation catalyst complex including a Group 9 metal complexed with a phosphine-based ligand; a syngas surrogate including formic acid and an anhydride compound, which forms carbon monoxide in situ; and hydrogen, which may derive from the syngas surrogate or not derived from the syngas surrogate. The method involves reacting the olefin substrate with a syngas surrogate in the presence of a hydroformylation catalyst complex, wherein the syngas surrogate forms carbon monoxide, and optionally hydrogen, in situ, and then isolating the aldehyde compound from a reaction mixture.

17 Claims, No Drawings

(56) References Cited

OTHER PUBLICATIONS

Borner, et al.: "Hydroformylation: Fundamentals, Processes, and Applications in Organic Synthesis", Wiley-VCH Verlag Gmbh & Co., (2016), vol. 1, Chapter 1, pp. 5-69 and Chapter 3 pp. 267-282; 2016.
Simonato; "New Efficient Catalytic System for Hydroxycarbonylation without CO Gas.", Journal of Molecular Catalysis A: Chemical, vol. 197 (2003) pp. 61-64.
Jenner: "Ruthenium Catalyzed Hydroformylation Reactions Using in situ Generation of Synthesis Gas from Aqueous Methyl Formate.", Applied Catalysis, vol. 75 (Apr. 5, 1991), pp. 289-298.
Konishi, et al.; "Palladium-catalyzed External CO-Free Carbonylation of Aryl Bromides Using 2,4,6-Trichlorophenyl Formate." Chem. Pharm. Bull. vol. 66, No. 5 (Feb. 14, 2018), pp. 562-567.
Schierz; "The Catalytic Decomposition of Formic Acid in Acetic Anhydride." J. Am. Chem. Soc. (Aug. 21, 1922), vol. 45, pp. 455-468.
Hood, "Cationic Cobalt (II) Hydroformylation" (03-18-019). LSU Doctoral Dissertations. 4882., https://digitalcommons.lsu.edu/gradschool_dissertations/4882.

* cited by examiner

HYDROFORMYLATION CATALYST SYSTEM WITH SYNGAS SURROGATE

FIELD OF THE INVENTION

The present invention relates to the preparation of aldehydes from olefins, and more particularly to preparing aldehydes from olefins using a syngas surrogate in the presence of a Group 9 metal catalyst.

BACKGROUND OF THE INVENTION

Carbonylation generally refers to a group of closely connected reactions in which a molecule of carbon monoxide (CO) is incorporated into a substrate. Hydroformylation, which is a type of carbonylation reaction, was discovered accidently in 1938 by Otto Roelen. The conventional reaction procedure of hydroformylation of terminal olefins is characterized by the use of a mixture of elemental hydrogen ($H_2$) and carbon monoxide (CO) (generally referred to as synthesis gases or syngas), at elevated pressure in the presence of a transition metal (e.g., Groups 7-10) catalyst thereby forming aldehydes. Hydrogen ("hydro") and a formyl group (H—C═O) are added in an atom-economical manner (Scheme 1) to the olefin. Unless ethylene is used as a substrate, the reaction can lead to a mixture of isomeric products, n-aldehydes (linear), and iso-aldehydes (branched). Because double-bond isomerization (often dependent on catalyst species) of the substrate may occur prior to the hydroformylation, different branched aldehydes can also be formed even when a single terminal olefin has been subjected to the reaction. Besides the rate of the reaction, the ratio of the isomers (regioselectivity) is therefore an important parameter of each hydroformylation.

SCHEME 1

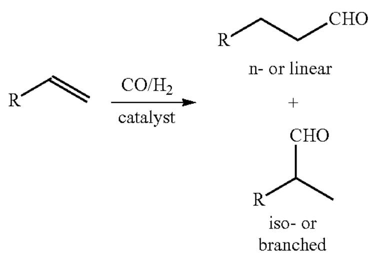

Traditionally, industrial carbonylation processes make use of highly toxic and flammable gaseous carbon monoxide. In fact, these properties (toxicity/flammability) impede the wider use of carbonylation reactions in industry and academia. Therefore, performing carbonylations without the use of gaseous CO is highly desirable.

Carbon monoxide (CO) surrogates in alkene carbonylation reactions have been reported intermittently in the last 30 years. Syngas surrogates include carbon dioxide, methanol, formaldehyde, formic acid, formates, formamide, and biomass (see Beller et al., *Angew. Chem. Int. Ed.* 2014, 53, 2-13). However, some of these syngas surrogates require separate reaction chambers or conversion catalysts, and/or the catalysts systems invoking these syngas surrogates yield undesirable linear/branched selectivity, require higher catalyst loadings, or lead to different functional groups (e.g., alcohols, carboxylic acids).

A recent report of a palladium-catalyzed hydroformylation of olefins using a syngas surrogate comprising 2 equivalents of formic acid and 1 equivalent of acetic anhydride produced a mixture of the linear/branched aldehydes, as well as the corresponding carboxylic acids (see Ren et al., *J. Am. Chem. Soc.* 2016, 138, 14864-14867.) Optimized conditions employing 1,3-bis(diphenylphosphino)propane (dppp) ligand, and tetrabutylammonium iodide (TBAI) additive in dichloroethane (DCE) solvent provided the corresponding linear aldehyde in modest yields and selectivity. In addition to the use potentially carcinogenic dichloroethane, the high catalyst loading (5 mol % Pd) is economically prohibitive on industrial scale, as attempts to perform subsequent hydroformylations using the recycled palladium catalyst provided diminished yields and/or selectivity.

In view of the foregoing, new hydroformylation catalyst systems and methods for hydroformylating olefins to form aldehydes are needed.

SUMMARY OF THE INVENTION

The present invention is premised on the realization that aldehyde compounds can be synthesized from olefin substrates without using a gaseous carbon monoxide source, and instead using a syngas surrogate comprising formic acid and anhydride compound, and hydrogen, in the presence of a hydroformylation catalyst complex comprising a Group 9 metal. The hydrogen is either derived from the syngas surrogate or not derived from the syngas surrogate.

Thus, in accordance with an embodiment of the present invention, a hydroformylation catalyst system useful for converting an olefin substrate to an aldehyde compound is provided. The hydroformylation catalyst system comprises (or consists essentially of) a hydroformylation catalyst complex comprising a Group 9 metal complexed with a phosphine-based ligand; and a syngas surrogate comprising formic acid and an anhydride compound, which in the presence of the hydroformylation catalyst complex forms carbon monoxide in situ, and hydrogen, which is either derived from the syngas surrogate in situ or not derived from the syngas surrogate.

In accordance with another embodiment of the present invention, a method of preparing an aldehyde compound is provided. The method comprising mixing an olefin substrate in a hydroformylation catalyst system to form a reaction mixture, wherein the hydroformylation catalyst system comprises (or consists essentially of) a hydroformylation catalyst complex and a syngas surrogate comprising formic acid and an anhydride compound, which in the presence of the hydroformylation catalyst complex forms carbon monoxide in situ, and hydrogen, which is either derived from the syngas surrogate in situ or not derived from the syngas surrogate. The hydroformylation catalyst complex comprises a Group 9 metal complexed with a phosphine-based ligand. The Group 9 metal is selected from the group consisting of cobalt, rhodium, and iridium, preferably rhodium. The method may further include isolating the aldehyde compound from the reaction mixture to provide an aldehyde product and a hydroformylation catalyst residue comprising the hydroformylation catalyst complex.

The objects and advantages of the present invention will be further appreciated in light of the following detailed description and examples.

DETAILED DESCRIPTION OF THE INVENTION

Therefore, keeping in mind the above problems occurring in the prior art, and it is an object of the present invention to provide a hydroformylation catalyst system comprising hydroformylation catalyst complex and a syngas surrogate, which is characterized by excellent catalytic activity and stability, and is capable of controlling the linear-branched (l/b) selectivity in the aldehyde product. It is a further object to provide a hydroformylation process using the same.

In accordance therewith, the present invention relates to a hydroformylation catalyst system and a hydroformylation process to produce aldehydes from olefin substrates using the same. More particularly, the hydroformylation catalyst system includes a hydroformylation catalyst complex comprising a Group 9 metal complexed with a phosphine-based ligand, and a syngas surrogate comprising formic acid and an anhydride compound, which in the presence of the hydroformylation catalyst complex forms carbon monoxide in situ, and hydrogen, which is either derived from the syngas surrogate in situ or not derived from the syngas surrogate. The syngas surrogate obviates the need to supply gaseous carbon monoxide to the hydroformylation catalyst system, but does not preclude the optional addition of hydrogen gas. Application of the hydroformylation catalyst system comprising the hydroformylation catalyst complex in the presence of the syngas surrogate to olefin substrates provides the desired aldehyde product with excellent catalytic activity and stability, as well as good linear/branched (l/b) selectivity.

In accordance with embodiments of the present invention, the hydroformylation catalyst complex comprises a Group 9 transition metal selected from the group consisting of cobalt, rhodium, and iridium.

In an embodiment, the Group 9 transition metal comprises cobalt. Exemplary forms of acceptable cobalt compounds includes, but are not limited to, dicobalt octacarbonyl $Co_2(CO)_8$, cobalt oxide $Co_2O_3$, cobalt carbonate $CoCO_3$, cobalt carboxylates $Co(RCOO)_2$, $Co_2(CO)_6(PnBu_3)_2$. $Co_2(CO)_6(P(OPh)_3)_2$ or a combination of them, more particularly $Co_2(CO)_8$. In another embodiment, the Group 9 transition metal comprises iridium. Exemplary forms of acceptable iridium compounds include, but are not limited to, Ir(acac)(COD), $HIr(CO)(PPh_3)_3$, $[Ir(COD)Cl]_2$, $Ir(COD)_2BF_4$ and $Ir_2(CO)_6(PPh_3)_2$, more particularly Ir(acac)(COD).

In yet another embodiment, the Group 9 transition metal comprises rhodium. Exemplary forms of acceptable rhodium compounds include, but are not limited to, rhodium complexes or rhodium salts of carboxylic acids, rhodium carbonyl species, rhodium halide species, rhodium alkoxide species, and/or rhodium organophosphine complexes. An example of rhodium carboxylate salt includes rhodium ethylhexanoate. Some examples of rhodium carbonyl species include rhodium (acetylacetonato)dicarbonyl ($Rh(acac)(CO)_2$), $Rh_4(CO)_{12}$, and $Rh_6(CO)_{16}$. An example of a rhodium halide species includes chloro(1,5-cyclooctadiene) rhodium dimer $[Rh(COD)Cl]_2$. An example of a rhodium alkoxide species includes methoxy(cyclooctadiene) rhodium dimer $[(MeO)Rh(COD)]_2$. An example of an rhodium organophosphine complex is tris(triphenylphosphine) rhodium carbonyl hydride $[RhH(CO)(PPh_3)_3]$ (where $Ph=C_6H_5$). In an embodiment, a suitable rhodium compound is selected from the group consisting of $Rh(acac)(CO)_2$, $[Rh(COD)Cl]_2$, and $[(MeO)Rh(COD)]_2$, more particularly $Rh(acac)(CO)_2$. In an embodiment, the hydroformylation catalyst may be selected from the group consisting of $Rh(acac)(CO)_2$, $[Rh(COD)Cl]_2$, and $[(MeO)Rh(COD)]_2$, Ir(acac)(COD), and $Co_2(CO)_8$.

Preferably, the content of the Group 9 metal is in the range of 0.00001 to 0.5 moles based on 1 mole of the olefin substrate (0.001 mol % to 50 mol %); more preferably in the range of 0.0001 to 0.1 (0.01 mol % to 10 mol %); and more preferably in the range of 0.0005 to 0.01 moles (0.05 mol % to 1 mol %) relative to 1 mole of olefin substrate. For example, based on the olefin substrate, the mole percentage of the Group 9 metal may be 0.001 mol %, 0.005 mol %, 0.01 mol %, 0.05 mol %, 0.1 mol %, 0.5 mol %, 1 mol %, 5 mol %, 10 mol %, 50 mol %, or 100 mol %, or in a range between any two of the foregoing.

In an embodiment, the Group 9 metal comprises cobalt. Preferably, the content of the cobalt is in a range of 0.00001 to 0.5 moles based on 1 mole of the olefin substrate (0.001 mol % to 50 mol %), and more preferably in the range of 0.0005 to 0.05 moles (0.05 mol % to 5 mol %) relative to 1 mole of olefin substrate. In another embodiment, the Group 9 metal comprises iridium. Preferably, the content of iridium is in a range of 0.00001 to 0.5 moles based on 1 mole of the olefin substrate (0.001 mol % to 50 mol %), and more preferably in the range of 0.0005 to 0.01 moles (0.05 mol % to 1 mol %) relative to 1 mole of olefin substrate. Preferably, in another embodiment, the Group 9 metal comprises rhodium. Preferably, the content of rhodium is in a range of 0.00001 to 0.5 moles based on 1 mole of the olefin substrate (0.001 mol % to 50 mol %), and more preferably in the range of 0.0005 to 0.01 moles (0.05 mol % to 1 mol %) relative to 1 mole of olefin substrate.

In accordance with embodiments of the present invention, the hydroformylation catalyst complex comprises a phosphine-based ligand, which forms a complex with the Group 9 metal. In one aspect, the phosphine-based ligand may be monodentate or bidentate, more particularly monodentate.

In an embodiment, the phosphine-based ligand is at least one compound of the general Formula (1) $PR^1R^2R^3$, where $R^1$, $R^2$, and $R^3$ are each independently selected from a substituted or unsubstituted alkyl group having 1 to 20 carbon atoms; a substituted or unsubstituted cycloalkyl group or cycloalkenyl group having 5 to 20 carbon atoms; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted hetero ring group having 4 to 36 carbon atoms, wherein the hetero alkyl group, the hetero aryl group, and the hetero ring group include one or more atoms that are selected from the group consisting of N, O, and S, and a substituent group is nitro ($-NO_2$), fluoride ($-F$), chloride ($-Cl$), bromide ($-Br$), or an alkyl group having 1 to 4 carbon atoms when $R^1$, $R^2$, and $R^3$ are substituted by the substituent group. More particularly, $R^1$, $R^2$, and $R^3$ are each independently selected from a substituted or unsubstituted aryl group having 6 to 36 carbon atoms. It is preferable that the monodentate phosphine ligand represented by the above Formula 1 be one or more selected from the group consisting of triphenylphosphine (TPP or $PPh_3$), tri(m-tolyl)phosphine (TMTP), diphenyl(p-tolyl)phosphine (DPPTP), tris(2,6-dimethoxyphenyl)phosphine (TDMPP), tris(4-methoxyphenyl)phosphine (TMPP), trimesitylphosphine (TMSTP), tris-3,5-xylylphosphine (TXP), tricyclohexylphosphine (TCHP), tribenzylphosphine (TBP), benzyl diphenylphosphine (BDPP), and diphenyl(2-methoxyphenyl)phosphine (DPMPP). More particularly, the monodentate phosphine ligand represented by the above Formula 1 is triphenylphosphine (TPP or $PPh_3$).

In another embodiment, the phosphine-based ligand is at least one compound of the general Formula (2) $R^1R^2P-R^4-PR^5R^6$, where $R^4$ is a hydrocarbon group with 2 to 20 carbon atoms, and $R^5$ and $R^6$ are each independently selected and defined identical to $R^1$ and $R^2$ above. It is preferable that the bi-dentate phosphine ligand represented by the above Formula 2 be one or more selected from the group consisting of 1,2-bis(diphenylphosphino)ethane (dppe); 1,2-bis(dimethylphosphino)ethane (dmpe); 1,3-bis (diphenylphosphino)propane (dppp); 1,4-bis(diphenylphosphino)butane (dppb); 1,5-bis(diphenylphosphino)pentane (dpppe); 1,6-bis(diphenylphosphino)hexane (dpph); 2,2'-Bis (diphenylphosphino)-1,1'-binaphthyl (binap); and combinations thereof. More particularly, the bidentate phosphine ligand represented by the above Formula 2 is 1,2-bis(diphenylphosphino)ethane (dppe).

Preferably, the content of the phosphine-based ligand in the hydroformylation catalyst system is in a range of 0.001 to 10 moles, based on 1 mole of the olefin substrate (i.e., 0.1 mol % to 1,000 mol %), such as 0.01 to 5 moles (i.e., 1 mol % to 500 mol %).

Alternatively, the content of the phosphine-based ligand may be expressed as a molar equivalent relative to the moles of Group 9 metal present in the catalyst system, and thus in the range of 1 to 500 moles, such as 2 to 250, 5 to 200, or 10 to 150, based on 1 mole of Group 9 metal. Thus, based on the Group 9 metal present in the catalyst complex, the molar equivalents of phosphine-based ligand may be 1, 2, 5, 10, 15, 25, 35, 50, 75, 100, 150, 200, 300, 400, 500, or in a range between any two of the foregoing. Non-limiting examples of phosphine-based ligand to Group 9 metal molar ratios include, but are not limited to, 1:1 to 500:1, 1:1 to 300:1, 1:1 to 200:1, 1:1 to 150:1, 1:1 to 100:1, 1:1 to 75:1, or 1:1 to 50:1.

Phosphine-based ligands can be susceptible to oxidation to their corresponding phosphine oxides, which appear to be ineffective ligands for the Group 9 metal-based hydroformylation catalyst. Oxidants such as molecular oxygen or peroxides are particularly effective at oxidizing phosphines into phosphine oxides. Accordingly, it is preferable to minimize the presence of adventitious oxygen in the hydroformylation reaction system. However, even if the hydroformylation reaction system is completely void of any adventitious oxygen, oxidation of phosphine ligand to the inactive phosphine oxide has been observed. Without being bound by any particular theory, it is believed that perhaps the phosphine ligand can also act as oxygen acceptor in the transformation of carbon dioxide ($CO_2$) into ligand carbon monoxide (CO), where the carbon dioxide ($CO_2$) arises from a Group 9 metal-catalyzed dehydrogenation reaction of formic ($HCO_2H$) acid into carbon dioxide ($CO_2$) and hydrogen ($H_2$).

Peroxides may be present in the hydroformylation reaction system by way of being an impurity in one or more of the hydroformylation reaction system components (e.g., olefin substrate or solvent). Accordingly, pretreatment of the olefin and/or solvent with an antioxidant, such as a saturated aqueous solution of sodium metabisulfite ($Na_2S_2O_5$), followed by distillation may be useful to substantially reduce or eliminate peroxide impurities. In an embodiment, the olefin substrate can be washed with a saturated aqueous solution of sodium metabisulfite, partitioned from the aqueous layer, and optionally distilled to remove any traces of water.

Nevertheless, conversion of the phosphine ligand into its inactive phosphine oxide may be offset by adding more of a suitable phosphine ligand (same or different) over the course of the reaction. Alternatively, the reaction may be initiated with an abundance of the phosphine-based ligand in the hydroformylation catalyst system to ensure a sufficient quantity of phosphine-based ligand is present throughout the entire course of the olefin conversion to aldehyde and thereby maintain a desirable level of catalyst complex activity and selectivity.

In a preferred embodiment, the hydroformylation catalyst complex comprises rhodium and the phosphine-based ligand. Preferably rhodium is provided as a rhodium compound selected from the group consisting of $Rh(acac)(CO)_2$, $[Rh(COD)Cl]_2$, and $[(MeO)Rh(COD)]_2$, more particularly $Rh(acac)(CO)_2$; and the phosphine-based ligand is a monodentate triaryl phosphine, such as triphenylphosphine (TPP), or a bidendate diarylalkyl phosphine, such as 1,2-bis(diphenylphosphino)ethane (dppe). In connection with this, when the total content of the monodentate phosphine-based ligand at the beginning of the reaction is less than 10 moles based on 1 mole of rhodium and its slow oxidation was not offset by addition of more phosphine-based ligand, diminished conversion and/or selectivity was observed. Accordingly, in an embodiment, the initial molar ratio of the monodentate phosphine ligand to rhodium is at least 10:1, such as at least 15:1, at least 20:1, at least 25:1, at least 30:1, at least 35:1, at least 40:1, at least 50:1, at least 75:1, at least 100:1, or at least 200:1 or in a range between any two of the foregoing. If the total molar ratio of the above phosphine-based ligand to rhodium is more than 500, cost is increased without an apparent additional benefit.

No special provisions are required for the preparation of the hydroformylation catalyst complex employed in the practice of the present invention, although it is preferred, for high catalyst activity, that all manipulations of the Group 9 metal and phosphine-based ligand components be carried out under an inert atmosphere, e.g., $N_2$, Ar, and the like. The desired quantities of a suitable Group 9 metal compound and the phosphine-based ligand are charged to the reactor in a suitable solvent. The sequence in which the various catalyst components are charged to the reactor is not critical. Thus, the Group 9 metal compound can be added to the reactor, then the phosphine-based ligand; or conversely, the phosphine-based ligand can be added to the reactor, then the Group 9 metal compound; or, alternatively, a preformed Group 9 metal-phosphine-based ligand complex can be charged to the reactor.

Embodiments of the present invention further provide a syngas surrogate including formic acid and an anhydride, which in the presence of the hydroformylation catalyst complex forms carbon monoxide in situ, and hydrogen, which is either derived from the syngas surrogate in situ or not derived from the syngas surrogate. The formic acid and anhydride should be sufficiently pure and free of any impurities that could poison the active catalytic species. Advantageously, the formic acid and the anhydride may be distilled prior to use.

Formic acid is hygroscopic and thus the moisture content should be minimized, so as to avoid hydrolyzing the anhydride compound. For example, formic acid may be characterized having a moisture content less than 5 wt %, such as 2 wt % or less.

The anhydride is selected from a compound having a general Formula (3) ($(R^7C{=}O){-}O{-}(O{=}CR^8)$), where $R^7$ and $R^8$ are independently selected from a substituted or unsubstituted alkyl or a substituted or unsubstituted aryl, where the substituent group may be a nitro ($-NO_2$), fluoride ($-F$), chloride ($-Cl$), bromide ($-Br$), or an alkyl group having 1 to 4 carbon atoms. Non-limiting examples of symmetric anhydrides (where $R^7$ and $R^8$ are the same) include acetic anhydride, propionic anhydride, butyric anhydride, isobutyric anhydride, pentanoic (valeric) anhydride, 3-methylbutyric (isovaleric) anhydride, and hexanoic anhydride. In an embodiment, the anhydride is selected from the group consisting of acetic anhydride, proprionic anhydride, isovaleric anhydride, and combinations thereof. In a preferred embodiment, the anhydride comprises acetic anhydride.

Based on the olefin substrate, the quantity of formic acid in the reaction mixture may be between 1 and 10 equivalents, preferably between 1.1 to 3 equivalents; and the quantity of acetic anhydride may be between 1 to 5 equivalents, preferably between 1.1 and 1.5 equivalents. In an embodiment, a mole ratio between formic acid and the anhydride is in a range from 1:1 to 4:1, preferably between 1:1 to 5:2.

Without being bound by any particular theory, it is believed that formic acid and the anhydride react to form a mixed anhydride, which under the hydroformylation reaction conditions decomposes in situ to form the required carbon monoxide reactant for the hydroformylation reaction and a carboxylic acid. In the case where the anhydride is acetic anhydride, the mixed anhydride is formic acetic anhydride. The in situ generated carbon monoxide binds to the Group 9 metal center of the active catalyst complex and eventually incorporates into the olefin substrate to form the desired aldehyde.

When formic acid is present in a stoichiometric excess relative to the anhydride (i.e., the mole ratio of formic acid to anhydride is greater than one) in the syngas surrogate, the required hydrogen ($H_2$) reactant for the hydroformylation reaction is also generated in situ, presumably from the Group 9-catalyzed dehydrogenation of formic acid, along with carbon dioxide ($CO_2$). If the stoichiometric excess formic acid is at least equimolar to the olefin substrate (e.g., 2 equivalents of formic acid and 1 equivalent of anhydride, based on the olefin substrate), then a separate supply of hydrogen should not be necessary to effect full or substantially full conversion of the olefin substrate. However, if the amount of formic acid is insufficient to generate the requisite hydrogen ($H_2$) reactant, then hydrogen pressure should be supplied to the reaction vessel. Excessive hydrogen pressure (e.g., >100 bar) prior to generating carbon monoxide may increase the hydrogenation side reaction pathway. In an embodiment, the mole ratio of formic acid to anhydride in the syngas surrogate is one or less, and thus hydrogen gas pressure is applied to the reaction vessel. Thus, the reaction vessel may be charged with hydrogen pressure to 25 bar or less, such as 20 bar, 15 bar, 10 bar, 4 bar, or 1 bar. For example, in an embodiment, each of the formic acid and the anhydride are present in the hydroformylation catalyst system in 1.1 equivalents, based on the olefin substrate, and an external supply of hydrogen gas (e.g., in a range of 1 to 20 bar, preferably in a range of 4 to 10 bar) is applied to a sealed reaction vessel prior to heating.

In the above hydroformylation process, it is preferable that the above olefin substrate be a mono- or di-substituted olefin substrate. In an embodiment, the olefin substrate is a mono-substituted olefin substrate (i.e., an alpha-olefin). In an embodiment, the olefin substrate is di-substituted olefin substrate. In another embodiment, the olefin substrate is represented by the following Formula (4):

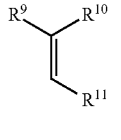

wherein $R^9$, $R^{10}$, and $R^{11}$ are each independently selected from the group consisting of hydrogen, a substituted or unsubstituted alkyl group having 1 to 20 carbon atoms; a substituted or unsubstituted alkenyl group having 1 to 20 carbon atoms, wherein the alkyl substituent group or alkenyl substituent group are selected from the group consisting of fluoride (F), a chloride (Cl), a bromide (Br), a trifluoromethyl group ($CF_3$); and a substituted or unsubstituted aryl group having 6 to 20 carbon atoms, wherein the aryl substituent group of the aryl group may be selected from the group consisting of nitro ($NO_2$), fluoride (F), chloride (Cl), bromide (Br), a methyl group, an ethyl group, a propyl group, and a butyl group, wherein at least one of $R^9$, $R^{10}$, or $R^{11}$ is hydrogen. In another embodiment, at least one of $R^9$, $R^{10}$, or $R^{11}$ is not hydrogen. In another embodiment, $R^{11}$ is hydrogen, and $R^9$ and $R^{10}$ are not hydrogen. In yet another embodiment, $R^{10}$ and $R^{11}$ are hydrogen, and $R^9$ is not hydrogen. In yet another embodiment, $R^9$ or $R^{10}$ is hydrogen, and $R^{11}$ is not hydrogen.

Non-limiting examples of suitable olefin substrates include one or more compounds selected from the group consisting of 1,4-dimethyl-4-vinyl-cyclohexene; cyclohexene; 1-hexene; ethyl cis-hex-3-enoate; 3,3-dimethyl-1-butene; 7-octenal; methyl 10-undecenoate; 4-tert-butyl-styrene; 5,7-dimethyl-oct-1,6-diene; and limonene. In an embodiment, the olefin substrate is selected from the group consisting of 1,4-dimethyl-4-vinyl-cyclohexene; cyclohexene; ethyl cis-hex-3-enoate; 3,3-dimethyl-1-butene; 7-octenal; methyl 10-undecenoate; 5,7-dimethyl-oct-1,6-diene, and limonene.

In the above hydroformylation process, the reaction mixture may be run neat (i.e., without any solvent) or in the presence of an organic solvent, such that the concentration of the olefin substrate in the reaction mixture is greater than about 0.1 molar (M), such as in a range between about 1 M to about 4 M. Examples of the suitable organic solvents include, but are not limited to, ethers such as tetrahydrofuran, 2-methyltetrahydrofuran, anisole, dimethoxyethane, and/or dioxane; aldehydes such as propionaldehyde, butyraldehyde, pentylaldehyde, and/or valeraldehyde; ketones such as acetone, methyl ethyl ketone, methyl isobutyl ketone, acetophenone, and/or cyclohexanone; aromatics such as benzene, toluene, and/or xylene; carboxylic acids such as acetic acid; amides such as dimethylformamide, dimethylacetamide, or n-methyl-2-pyrrolidone; halogenated aromatics such as orthodichlorobenzene; halogenated paraffins such as methylene chloride; and/or paraffin hydrocarbons such as cyclohexane and/or heptane. Preferably, the solvent comprises an ether, such as 2-methyltetrahydrofuran (2-MeTHF).

In the hydroformylation process, a preferable reaction temperature and reaction pressure may include those known in the art. For example, the present hydroformylation process can be performed in a sealed vessel at a reaction temperature in the range of preferably about 20° C. to 200° C., more preferably about 50° C. to 150° C., and most preferably about 60° C. to 130° C. If the hydroformylation catalyst system further comprises hydrogen gas not derived from the syngas surrogate, the vessel may be charged with the hydrogen gas to a desired pressure prior to heating the reaction mixture to the desired reaction temperature. For example, the hydrogen gas charge to the reaction vessel may be in a range from about atmospheric to less than 100 bar, preferably between 1 bar and 25 bar. Hydrogen gas can be supplied during the course of the reaction in order to maintain a desired pressure.

In order to perform the above hydroformylation reaction, the desired quantities of the hydroformylation catalyst system components (i.e., the Group 9 metal compound, the phosphine-based ligand, the olefin substrate, the anhydride compound, formic acid, and optionally hydrogen gas and/or the organic solvent) are introduced to a sealable reaction vessel (e.g., autoclave), which is subsequently sealed, agitated, and heated to perform the hydroformylation reaction. Upon heating to a sufficient temperature to initiate the generation of CO, and optionally $H_2$, from the syngas surrogate, pressure in the hydroformylation reaction system initially rises, and then system pressure decreases as the reactant gases ($CO/H_2$) react with the olefin substrate forming the desired aldehyde compound.

In accordance with an aspect of the present invention, hydroformylation catalyst complex is recyclable and maintains satisfactory conversion and selectivity through multiple batch runs. These characteristics arise from the maintenance of the appropriate ratio of phosphine ligand to Group 9 metal over the course of the hydroformylation reaction. The slow conversion of the phosphine ligand into its inactive phosphine oxide may be offset by adding more of a suitable phosphine ligand (same or different) over the course of the reaction or by starting the reaction with a substantial excess of the phosphine ligand. In an embodiment, the molar ratio of phosphine-based ligand to Group 9 metal is at least 1:1, such as 2:1, 5:1, 10:1, 20:1 or more, 40:1 or more, 50:1 or more, or 100:1 or more. In an embodiment, the Group 9 metal is rhodium and the molar ratio of phosphine-based ligand to rhodium is in a range from 2:1 to 20:1.

In an embodiment, the amount of phosphine ligand remaining in the hydroformylation reaction mixture at the end of the reaction is quantified. Quantification may be achieved by a variety of analytical techniques (e.g., GC, HPLC, NMR, etc.) using the appropriate standards. In order to ensure that a sufficient quantity of phosphine ligand is present in the recycled hydroformylation catalyst mixture, the amount of phosphine ligand lost due to its conversion to the phosphine oxide may be added to the reaction mixture prior to isolating the aldehyde product from the catalyst.

For example, in an embodiment, the desired quantity of phosphine ligand is added to the end-of-reaction mixture, and then the reaction mixture is distilled to recover solvent, starting olefin substrate (if any), aldehyde product, and/or impurities. For example, the solvent may be recovered by distillation at a first temperature/pressure condition, followed by recovery of the aldehyde product at a second temperature/pressure condition. The distillation residue remaining after recovery of the solvent/aldehyde may then be mixed with a second batch of olefin substrate, formic acid, anhydride compound, and optionally solvent and/or hydrogen gas for another batch hydroformylation run.

Advantageously, the hydroformylation catalyst system and method described herein may be applied in the manufacture of one or more valuable aldehyde compounds, which may useful compounds themselves, such as fragrance molecules. In accordance with an embodiment, a product comprising an aldehyde is provided, where the aldehyde is formed by the hydroformylation of an olefin using the hydroformylation catalyst system described herein, where the olefin is selected from the group consisting of 1,4-dimethyl-4-vinyl-cyclohexene; cyclohexene; 1-hexene; ethyl cis-hex-3-enoate; 3,3-dimethyl-1-butene; 7-octenal; methyl 10-undecenoate; 5,7-dimethyl-oct-1,6-diene; 4-tert-butyl-styrene; and limonene; and where the aldehyde is selected from the group consisting of 3-(1,4-dimethyl-3-cyclohexen-1-yl)propionaldehyde; cyclohexanecarbaldehyde; ethyl 3-formylhexanoate and/or ethyl 4-formylhexanoate; 4,4-dimethylvaleraldehyde; azelaaldehyde; methyl 11-formylundecanoate; 6,8-dimethyl-7-nonenal; 3-[p-(tert-butyl)phenyl]propionaldehyde; and p-menth-1-ene-9-carbaldehyde, respectively.

The aldehydes derived from the hydroformylation catalyst system and method described herein may also be useful chemical intermediates for the manufacture of other valuable molecules, such as pharmaceuticals, flavors, or fragrances. For example, perfumery compound 6,8-dimethyl-non-7-enal, which is described in WO2006077305 by Jaunky et al., was prepared by the hydroformylation of 5,7-dimethyl-octa-1,6-diene using the hydroformylation catalyst system in good yield. And the hydroformylation of DMVCH in accordance with embodiments of the present invention provides aldehyde 3-(1,4-dimethyl-3-cyclohexen-1-yl)propionaldehyde, which can be further transformed into various aroma chemicals, such as 6-(1,4-dimethylcyclohex-1-en-4-yl)hex-3-en-2-one; (2,5-dimethylbicyclo[3,3,1]non-2-en-8-yl)acetone; 6-(1,4-dimethylcyclohex-1-en-4-yl)hex-4-en-2-one; or (2,6-dimethylbicyclo-[3,3,1]non-2-en-8-yl) acetone, as described in GB1471856A to Aalderht Johannes de Jong. In accordance with another embodiment of the present invention, a method is provided for preparing 6,8-dimethyl-non-7-enal, comprising treating the olefin substrate 5,7-dimethyl-octa-1,6-diene with the hydroformylation catalyst complex and syngas surrogate.

Thus, in accordance with an embodiment of the present invention, a hydroformylation catalyst system is provided, which is useful for converting an olefin substrate to an aldehyde compound, the system comprising: a hydroformylation catalyst complex comprising a Group 9 metal complexed with a phosphine-based ligand, wherein the Group 9 metal is selected from the group consisting of cobalt, rhodium, and iridium, preferably rhodium; and a syngas surrogate comprising formic acid and an anhydride compound, which in the presence of the hydroformylation catalyst complex forms carbon monoxide, and optionally hydrogen, in situ.

In another embodiment, the catalyst system as set forth above, wherein the Group 9 metal comprises rhodium. In another embodiment, the catalyst system as set forth in any system described above, wherein the Group 9 metal comprises rhodium provided within a rhodium compound selected from the group consisting of $Rh(acac)(CO)_2$, $[Rh(COD)Cl]_2$, and $[(MeO)Rh(COD)]_2$. In another embodiment, the catalyst system as set forth in any system described above, wherein the phosphine-based ligand is selected from the group consisting of a monodentate phosphine ligand, a bidentate phosphine ligand, or a combination thereof. In another embodiment, the catalyst system as set forth in any system described above, wherein the phosphine-based ligand is a monodentate phosphine ligand comprising at least one compound of the general formula (1):

$$PR^1R^2R^3 \quad (1)$$

where $R^1$, $R^2$, and $R^3$ are each independently selected from a substituted or unsubstituted alkyl group having 1 to 20 carbon atoms;

a substituted or unsubstituted cycloalkyl group or cycloalkenyl group having 5 to 20 carbon atoms;

a substituted or unsubstituted aryl group having 6 to 36 carbon atoms;

a substituted or unsubstituted heteroalkyl group having 1 to 20 carbon atoms;

a substituted or unsubstituted heteroaryl group having 4 to 36 carbon atoms; or a substituted or unsubstituted hetero ring group having 4 to 36 carbon atoms, wherein the hetero alkyl group, the hetero aryl group, and the hetero ring group includes one or more atoms that are selected from the group consisting of N, O, and S;

wherein a substituent group is selected from the group consisting of nitro (—$NO_2$), fluoride (—F), chloride (—Cl), bromide (—Br), and an alkyl group having 1 to 4 carbon atoms, when $R^1$, $R^2$, and $R^3$ are substituted by the substituent group.

In another embodiment, the catalyst system as set forth in any system described above, wherein the phosphine-based ligand is a bidentate phosphine ligand comprising at least one compound of the general formula (2):

$$R^1R^2P—R^4—PR^5R^8 \quad (2)$$

where $R^1$, $R^2$, $R^5$, and $R^8$ are each independently selected from a substituted or unsubstituted alkyl group having 1 to 20 carbon atoms;

a substituted or unsubstituted cycloalkyl group or cycloalkenyl group having 5 to 20 carbon atoms;

a substituted or unsubstituted aryl group having 6 to 36 carbon atoms;

a substituted or unsubstituted heteroalkyl group having 1 to 20 carbon atoms;

a substituted or unsubstituted heteroaryl group having 4 to 36 carbon atoms; or a substituted or unsubstituted hetero ring group having 4 to 36 carbon atoms, wherein the hetero alkyl group, the hetero aryl group, and the hetero ring group includes one or more atoms that are selected from the group consisting of N, O, and S;

wherein a substituent group is selected from the group consisting of nitro (—$NO_2$), fluoride (—F), chloride (—Cl), bromide (—Br), and an alkyl group having 1 to 4 carbon atoms, when $R^1$, $R^2$, $R^4$, and $R^6$ are substituted by the substituent group; and where $R^4$ is a hydrocarbon group with 2 to 20 carbon atoms.

In another embodiment, the catalyst system as set forth above, wherein the anhydride compound comprises a compound having a general formula (3):

$$(R^7C{=}O)—O—(O{=}CR^8) \quad (3)$$

where $R^7$ and $R^8$ are independently selected from a substituted or unsubstituted alkyl or a substituted or unsubstituted aryl, where the substituent group may be a nitro (—$NO_2$), fluoride (—F), chloride (—Cl), bromide (—Br), or an alkyl group having 1 to 4 carbon atoms.

In another embodiment, the catalyst system as set forth in any system described above, wherein a molar ratio of formic acid to anhydride is in a range from 1:1 to 4:1. In another embodiment, the catalyst system as set forth in any system described above, further comprising hydrogen gas not derived from the syngas surrogate.

In another embodiment, the catalyst system as set forth in any system described above, wherein the Group 9 metal comprises rhodium, and wherein a molar ratio of rhodium to phosphine-based ligand is in a range of 1:1 to 1:500. One or more of the foregoing hydroformylation catalyst systems are useful in a method for preparing aldehyde compounds from olefin substrates.

Thus, in accordance with yet an embodiment of the present invention, a method of preparing an aldehyde compound is provided, comprising: mixing an olefin substrate in a hydroformylation catalyst system to form a reaction mixture, wherein the hydroformylation catalyst system comprises a hydroformylation catalyst complex and a syngas surrogate, wherein the hydroformylation catalyst complex comprises a Group 9 metal complexed with a phosphine-based ligand, wherein the syngas surrogate comprises formic acid and an anhydride compound, and wherein the Group 9 metal is selected from cobalt, rhodium, and iridium, preferably rhodium; and isolating the aldehyde compound from the reaction mixture to provide an aldehyde product and a hydroformylation catalyst residue comprising the hydroformylation catalyst complex.

In another embodiment, the method as set forth above, wherein isolating the aldehyde compound comprises distilling the aldehyde compound from the reaction mixture and provides an aldehyde product and an undistilled fraction comprising the hydroformylation catalyst residue. In another embodiment, the method as set forth in any of the methods described above, further comprising: mixing a second olefin substrate with the hydroformylation catalyst residue and the syngas surrogate to form a second reaction mixture. In another embodiment, the method as set forth in any of the methods described above, wherein a portion of the phosphine-based ligand is converted to its corresponding phosphine oxide, the method further comprising adding a quantity of the phosphine-based ligand to the second reaction mixture to offset at least of portion that was converted to the corresponding phosphine oxide.

In yet another embodiment, the method as set forth in any of the methods described above, wherein a molar ratio of formic acid to anhydride is in a range from 1:1 to 4:1. In yet another embodiment, the method as set forth in any of the methods described above, further comprising providing hydrogen gas not derived from the syngas surrogate.

In yet another embodiment of the present invention, using the catalyst system as set forth in any embodiment described above, in any of the methods described above, for preparing the aldehyde compound, comprising: mixing the hydroformylation catalyst system of the invention with the olefin substrate to form a reaction mixture in a sealed reaction vessel; and reacting the olefin substrate with carbon monoxide and hydrogen in the presence of the hydroformylation catalyst complex.

In yet another embodiment of the present invention, in any of the methods described above, for preparing the aldehyde compound, comprising: isolating the aldehyde compound from the reaction mixture to provide the aldehyde product and a hydroformylation catalyst residue. In yet another embodiment of the present invention, in any of the methods described above, wherein isolating the aldehyde compound comprises distilling the aldehyde compound from the above-mentioned reaction mixture (referred hereinbelow to as "the first reaction mixture") to provide the aldehyde product and an undistilled fraction comprising the hydroformylation catalyst residue.

In yet another embodiment of the present invention, in any of the methods described above, for preparing the aldehyde compound, comprising: recycling the hydroformylation catalyst residue by combining with additional quantities of a second olefin substrate and the syngas surrogate comprising formic acid and the anhydride compound, and optionally hydrogen gas, to form a second reaction mixture; and reacting the second olefin substrate with carbon monoxide produced from the syngas surrogate, and hydrogen gas, which is either derived from the syngas surrogate or not derived from the syngas surrogate, in the presence of the hydroformylation catalyst residue to form the aldehyde compound in the second reaction mixture.

In yet another embodiment of the present invention, in any of the methods described above, for preparing the aldehyde compound, wherein a portion of the phosphine-based ligand is converted to its corresponding phosphine oxide, the process further comprising quantifying the phosphine-based ligand and/or the corresponding phosphine oxide, and determining a molar ratio of the Group 9 metal to the phosphine-based ligand prior to and/or after isolating the aldehyde compound from the first and/or second reaction mixture.

In yet another embodiment of the present invention, in any of the methods described above, for preparing the aldehyde product, further comprising adding a sufficient quantity of the phosphine-based ligand to the hydroformylation catalyst system to adjust the molar ratio of Group 9 metal to phosphine-based ligand in a range from 1:5 to 1:500, prior to and/or after isolating the aldehyde compound from the first reaction mixture.

In yet another embodiment of the present invention, using the catalyst system as set forth in any embodiment described above, in any of the methods described above, for preparing a fragrance product comprising the aldehyde compound or a derivative thereof, the use comprising: mixing the hydroformylation catalyst system of the invention with the olefin substrate in a sealed reaction vessel; and reacting the olefin substrate with carbon monoxide produced from the syngas surrogate, and hydrogen gas, which is either derived from the syngas surrogate or not derived from the syngas surrogate, in the presence of the hydroformylation catalyst complex to form the aldehyde compound; isolating the aldehyde compound; and optionally further reacting the aldehyde compound to form a derivative thereof; and combining the isolated aldehyde compound or the derivative thereof with one or more fragrant compound(s) to obtain the fragrance product.

Hereinafter, embodiments of the present invention will be described in detail in light of Examples. The present invention may, however, be embodied in many different forms and should not be construed as being limited to the Examples set forth herein. Rather, these Examples are provided such that this disclosure will be thorough and complete and will fully convey the concept of the present invention to those skilled in the art.

EXAMPLES

Example 1: Various reaction conditions were investigated for effecting the hydroformylation of 1,4-dimethyl-4-vinylcyclohexene (DMVCH) using the syngas surrogate comprising formic acid and anhydride compounds. A summary of the reaction details and results are shown in Table 1. Mole percentages (mol %) of catalyst and ligand, and equivalents (eq. or equiv.) of reactants are based relative to the moles of olefin substrate.

TABLE 1

Hydroformylation reaction systems using syngas surrogate.

| Entry | Metal | Compound (mol %) | P Ligand (mol %) | Anhydride (equiv) | Formic acid (equiv) | Conv. (GC %) | Selectivity (GC %) | l:b |
|---|---|---|---|---|---|---|---|---|
| a1 | Pd | $Pd(OAc)_2$ (5) | dppp (5) | acetic (3.0) | (4.0) | 89 | 76 | >99:1 |
| a2 | Pd | $Pd(OAc)_2$ (0.1) | dppp (0.2) | acetic (3.0) | (4.0) | <3 | — | — |
| b | Ru | $Ru_3(CO)_{12}$ (0.1) | TPP (10) | acetic (1.1) | (2.2) | <1 | — | — |
| c | Ru | $RuCl_2(CO)_2(PPH_3)_2$ (0.1) | TPP (10) | acetic (1.1) | (2.2) | <1 | — | — |
| d | Rh | $[RhCl(COD)]_2$ (0.1) | TPP (10) | acetic (1.1) | (2.2) | 91 | 95 | 99:1 |
| e | Rh | $[(MeO)Rh(COD)]_2$ (0.1) | TPP (10) | acetic (1.1) | (2.2) | 75 | 92 | 99:1 |
| f | Rh | $Rh(acac)(CO)_2$ (0.4) | dppe (0.5) | acetic (1.1) | (2.2) | 98 | 89 | 98:2 |
| g | Rh | $Rh(acac)(CO)_2$ (0.1) | TPP (10) | acetic (1.1) | (2.2) | 90 | 94 | 99:1 |
| h | Rh | $Rh(acac)(CO)_2$ (0.1) | TPP (10) | propionic (1.1) | (2.2) | 82 | 93 | 99:1 |
| I | Rh | $Rh(acac)(CO)_2$ (0.1) | TPP (10) | isovaleric (1.1) | (2.2) | 88 | 94 | 99:1 |
| j | Rh | $Rh(acac)(CO)_2$ (0.1) | TPP (10) | succinic (1.1) | (2.2) | 7 | 63 | >99:1 |
| k | Ir | Ir(acac)(COD) (0.5) | dppe (0.5) | acetic (1.1) | (2.2) | 100 | 49 | 98:2 |

TABLE 1-continued

Hydroformylation reaction systems using syngas surrogate.

| Entry | Metal | Compound (mol %) | P Ligand (mol %) | Anhydride (equiv) | Formic acid (equiv) | Conv. (GC %) | Selectivity (GC %) | l:b |
|---|---|---|---|---|---|---|---|---|
| l | Co | $Co_2(CO)_8$ (5) | dppe (5) | acetic (1.1) | (2.2) | 89 | 50 | 97:3 |
| m | Co | $Co_2(CO)_8$ (5) | TPP (10) | acetic (1.1) | (2.2) | 20 | 66 | 97:3 |

a1) DMVCH (5 g), 2.5 mol % TBAI, DCE, 80° C., 24 h;
a2) DMVCH (5 g), 0.05 mol % TBAI, DCE, 80° C., 22 h;
b-c) DMVCH (7 g), 2-MeTHF, 90° C., 22 h then 130° C. 2 h;
d) DMVCH (7 g), 2-MeTHF, 90° C., 22 h;
e) DMVCH (7 g), 2-MeTHF, 90° C., 3 h;
f) DMVCH (7 g), 2-MeTHF, 90° C., 24 h;
g) DMVCH (30 g), 2-MeTHF, 90° C., 24 h;
h-j) DMVCH (7 g), 2-MeTHF, 90° C., 24 h;
k) DMVCH (7 g), 2-MeTHF, 130° C., 19 h;
l) DMVCH (7 g), 2-MeTHF, 130° C., 16 h;
m) DMVCH (7 g), 2-MeTHF, 130° C., 22 h.

Comparative example (entry a1) utilized palladium acetate to effect the hydroformylation of 1,4-dimethyl-4-vinylcyclohexene (DMVCH) under the optimized conditions reported in prior art publication Ren et al., *J. Am. Chem. Soc.* 2016, 138, 14864-14867 (Table 1, entry 15, e.g., 5 mol % Pd, dichlorethane solvent, tetrabutylammonium iodide additive). Reducing the catalyst loading to 0.1 mol % (based on the DMVCH substrate) resulted in little conversion after 22 hours (entry a2). Attempts to effect the hydroformylation of DMVCH with two different ruthenium compounds (comparative examples of entries b and c) failed to form any of the corresponding aldehyde.

In entries d through j, various rhodium-containing hydroformylation catalyst complexes were investigated for the hydroformylation of 1,4-dimethyl-4-vinylcyclohexene (DMVCH). In entries g through j, various anhydride compounds were studied in a rhodium-based hydroformylation catalyst system. In entry k through entry m, iridium- and cobalt-based hydroformylation catalyst complexes were investigated for the hydroformylation of DMVCH. In these examples, the Group 9 metal compound, a phosphine-based ligand, DMVCH, solvent (2-MeTHF, 1M DMVCH), formic acid, and the anhydride compound were added to an autoclave, which was purged with nitrogen, sealed, and then stirred while heating to an elevated temperature. At the end of the reaction period, the reaction mixture was cooled, vented, and an aliquot analyzed by GC-FID (HP-DB1 (30 m, 0.25 mm, 0.25 μm), $H_2$ 1.4 mL/min, 50° C. to 250° C. at 50° C./min and 250° C. for 10 min). Conversion, selectivity, and linear:branched (l:b) ratios were determined by GC area percent (GC %). Overall, the Group 9 metal-based hydroformylation catalyst systems proved to be acceptable in conversion and selectivity, whereas the ruthenium-based catalyst failed to effect the desired hydroformylation.

Due to the high costs of precious metal catalysts, the recyclability of various hydroformylation catalyst complexes was further investigated (see Table 2). At the end of the initial reaction, the solvent, any unreacted starting materials, and reaction products were removed by distillation under reduced pressure. The undistilled fraction comprising the hydroformylation catalyst residue was combined with DMVCH, solvent (2-MeTHF, 1M DMVCH), formic acid (2.2 equiv), and the anhydride compound (1.1 equiv) in an autoclave, which was purged with nitrogen, sealed, and then stirred while heating to the desired reaction temperature. At the end of the reaction period, the reaction mixture was cooled, vented, and an aliquot analyzed by GC. The recycling process may be repeated, with or without adding more phosphine based ligand to offset any observed oxidation.

While a comparative experiment using a fresh palladium catalyst at relatively high loading (5 mol %) provided good conversion on initial reaction, the selectivity for the aldehyde product was modest (76%), and the recycled catalysts yield degraded in subsequent reactions. In contrast, recycled rhodium catalyst maintained its high conversion (>90%) and selectivity (94%) (see Table 2). Non-optimized experiments run with other Group 9 metals (i.e., iridium and cobalt) showed good conversion with modest selectivity for the desired aldehyde. But in these Ir and Co examples, excellent linear:branch (l:b) selectivity was achieved.

TABLE 2

Recycling runs of various hydroformylation catalysts.

| Metal | Entry | Conversion (GC %) | Selectivity (GC %) | Linear:Branched |
|---|---|---|---|---|
| $Pd(OAc)_2$ | Initial test Pd[a] | 89 | 76 | >99:1 |
| | Recycle 1 | 96 | 54 | >99:1 |
| | Recycle 2 | 84 | 31 | >99:1 |
| $Rh(acac)(CO)_2$ | Initial test Rh[b] | 90 | 94 | 99:1 |
| | Recycle 1 | 90 | 94 | 99:1 |
| | Recycle 2 (+3.5 mol % $PPh_3$) | 94 | 94 | 99:1 |
| Ir(acac)(COD) | Initial test Ir[c] | 100 | 49[f] | 98:2 |
| Ir(acac)(COD) | Recycle 1 | 100 | 53[g] | 98:2 |
| $Co_2(CO)_8$ | Initial test Co[d] | 20 | 66 | 97:3 |
| $Co_2(CO)_8$ | Recycle 1 | 38 | 69 | 98:2 |
| $Co_2(CO)_8$ | Initial test Co[e] | 89 | 50 | 97:3 |
| $Co_2(CO)_8$ | Recycle 1 | 72 | 35 | 96:4 |

[a]DMVCH (5 g), $Pd(OAc)_2$ (5 mol %), dppp (10 mol %), TBAI (2.5 mol %), HCOOH (4 eq.), $Ac_2O$ (3 eq.), DCE (1M), 80° C., 24 h;
[b]DMVCH (30 g), $Rh(acac)(CO)_2$ (0.1 mol %), $PPh_3$ (10 mol %), HCOOH (2.2 eq.), $Ac_2O$ (1.1 eq.), 2-MeTHF (1M), 90° C., 24 h;
[c]Ir(acac)(COD) (0.5 mol %), dppe (0.5 mol %), HCOOH (2.2 eq.), $Ac_2O$ (1.1 eq.), 2-MeTHF (1M), 130° C., 19 h;
[d]$Co_2(CO)_8$ (5 mol %), $PPh_3$ (10 mol %), HCOOH (2.2 eq.), $Ac_2O$ (1.1 eq.), 2-MeTHF (1M), 130° C., 22 h;
[e]$Co_2(CO)_8$ (5 mol %), dppe (10 mol %), HCOOH (2.2 eq.), $Ac_2O$ (1.1 eq.), 2-MeTHF (1M), 130° C., 22 h;
[f]crude reaction mixture also contained 33% hydrogenated product; and
[g]crude reaction mixture also contained 26% hydrogenated product.

Example 2: In a 600 mL autoclave were introduced $Rh(acac)(CO)_2$ (0.057 g, 0.220 mmol), triphenylphosphine (5.78 g, 22.0 mmol), 2-methyltetrahydrofuran (2-MeTHF) (220 ml), dimethylvinylcyclohexene (DMVCH, 30 g, 220 mmol), formic acid (18.58 ml, 484 mmol) and acetic anhydride (22.85 ml, 242 mmol). The mixture was heated at 90° C. for 24 h. The pressure reached a maximum at 16 bar and the final pressure was 12 bar. The pressure was then released and the mixture transferred to a distillation apparatus. An aliquot was analyzed by GC to check the conversion, selectivity (GC %), and extent of phosphine ligand oxidation. The distillation commenced to recover solvent and isolate the aldehyde from the reaction mixture (see Table 3).

TABLE 3

Distillation of Example 2 reaction mixture from first run with fresh catalyst.

| Fraction | Pressure (mbar) | $T_{bath}$ (° C.) | $T_{boil}$ (° C.) | $T_{head}$ (° C.) | mass (g) | GC Purity |
|---|---|---|---|---|---|---|
| 1 | 190 | 90 | 42 | 35 | 160 | 2-MeTHF (88%) |
| 2 | 20 | 90 | 23 | 25 | 4 | 2-MeTHF (45%)<br>DMVCH (12%)<br>Aldehyde (7%) |
| 3 | 1.4 | 90 | 64 | 56 | 7 | Aldehyde (95%) |

Example 3: The distillation residue from Example 2 was then diluted with 2-MeTHF (220 ml), dimethylvinylcyclohexene (DMVCH, 30 g, 220 mmol) and transferred back to the 600 mL autoclave. Formic acid (18.58 ml, 484 mmol) and acetic anhydride (22.85 ml, 242 mmol) were added and the mixture was heated at 90° C. for 24 h. The pressure reached a maximum at 16 bar and the final pressure was 12 bar. The pressure was then released and the mixture transferred to a distillation apparatus. An aliquot was analyzed by GO to check the conversion, selectivity (GC %), and extent of phosphine ligand oxidation. Triphenylphosphine (2.022 g, 7.71 mmol) was added. Recovery of solvent and isolation of the aldehyde from the reaction mixture was again performed by distillation at reduced pressure (see Table 4).

TABLE 4

Distillation of Example 3 reaction mixture from second run with recycled catalyst.

| Fraction | Pressure (mbar) | $T_{bath}$ (° C.) | $T_{boil}$ (° C.) | $T_{head}$ (° C.) | mass (g) | GC Purity |
|---|---|---|---|---|---|---|
| 1 | 294-100 | 90 | 53-60-50 | 46-48 | 162 | 2-MeTHF (98%) |
| 2 | 100-18 | 90 | 58 | 45 | 15 | 2-MeTHF (61%)<br>DMVCH (31%)<br>Aldehyde (6%) |
| 3 | 0.9 | 90 | 62 | 56 | 42 | Aldehyde (96%) |

Example 4: The distillation residue from Example 3 was then diluted with 2-MeTHF (220 ml), dimethylvinylcyclohexene (DMVCH, 30 g, 220 mmol) and transferred back to the 600 mL autoclave. Formic acid (18.58 ml, 484 mmol) and acetic anhydride (22.85 ml, 242 mmol) were added and the mixture was heated at 90° C. for 24 h. The pressure reached a maximum at 16 bar and the final pressure was 12 bar. The pressure was then released and the mixture transferred to a distillation apparatus. An aliquot was analyzed by GC and gave 94% of conversion with 94% selectivity toward the aldehyde.

To demonstrate the general applicability of the hydroformylation catalyst system, the conditions from Example 2 were applied to a variety of olefin substrates (see Examples 5-15, Table 5). Conversion, selectivity, and linear:branched (l:b) ratios were determined by GC area percent.

TABLE 5

Hydroformylation[a] of various olefin substrates.

| # | Olefin substrate | Conversion (%) | Selectivity (%) | Linear:Branched |
|---|---|---|---|---|
| 5 | 1,4-dimethyl-4-vinyl-cyclohexene | 90 | 94 | 99/1 |
| 6 | cyclohexene[b] | 43 | 99 | n/a |
| 7 | 1-hexene | 99 | 73 | 77/23 |
| 8[d] | 1-methylcyclohexene | <1 | ~ | ~ |
| 9 | ethyl cis-hex-3-enoate | 89 | 99[c] | n/a |
| 10 | 3,3-dimethyl-1-butene | 99 | 96 | 98/2 |
| 11 | 7-octenal | 99 | 70 | 75/25 |
| 12 | methyl 10-undecenoate | 99 | 60 | 72/28 |
| 13 | 5,7-dimethyl-oct-1,6-diene | 99 | 66 | 74/26 |
| 14 | 4-tert-butyl-styrene | 99 | 38 | 38/62 |
| 15 | limonene | 62 | 95 | >99/1 |

[a]Olefin (1 equiv); $Rh(acac)(CO)_2$ (0.1 mol %); $PPh_3$ (10 mol %); $AC_2O$ (1.1 equivalents); $HCO_2H$ (2.2 equivalents); 2-methyltetrahydrofuran (1M olefin); 90° C., 13-19 h.
[b]130° C., 4 h.
[c]Merged for the 2 aldehyde regioisomers possibly formed;
[d]comparative example.

Under the general non-optimized conditions, excellent conversion was observed for mono-substituted, alpha olefin substrates, while modest to good conversions were observed for di-substituted olefins (1,1- or 1,2-substituted). However, tri-substituted olefins (comparative example 8) showed very little reactivity (<1%).

Example 16: Syngas surrogate and external hydrogen gas. Utilization of a syngas surrogate comprising equimolar amounts of formic acid and acetic anhydride and externally supplied hydrogen gas was screened against the model olefin substrate, 1,4-dimethyl-4-vinylcyclohexene (DMVCH), to evaluate conversion and selectivity to the corresponding aldehyde, as well as the extent of phosphine-based ligand oxidation. A rhodium-containing compound (0.1 mol % Rh), a monodentate phosphine-based ligand (10 mol %), DMVCH (1 equiv), solvent (2-MeTHF, 1M DMVCH), formic acid (1.1 equiv), and the anhydride (1.1 equiv) were added to an autoclave, which was purged with nitrogen, sealed, evacuated, and external hydrogen ($H_2$) gas pressure supplied to the system. At the end of the reaction period, the reaction mixture was cooled, vented, and an aliquot analyzed by GC-FID (HP-DB1 (30 m, 0.25 mm, 0.25 μm), $H_2$ 1.4 mL/min, 50° C. to 250° C. at 50° C./min and 250° C. for 10 min). Conversion, selectivity, amount of hydrogenation product, and extent of phosphine oxidation were determined by GC area percent.

TABLE 6

Hydroformylation using equimolar formic acid/anhydride and external $H_2$.

| No | $HCO_2H/Ac_2O$ (1.1:1.1) | $(PPh_3/Ph_3P{=}O)_{final}$ | Conversion (%) | Selectivity (%) | Hydrogenated DMVCH |
|---|---|---|---|---|---|
| 16a | $H_2$ (4 bar before heating) | 92/8 | 96[a] | 91 | 2% |
| 16b | $H_2$ (10 bar before heating) | 93/7 | 99[a] | 90 | 5% |
| 16c | $H_2$ (25 bar to 10 bar) | 92/8 | 63[b] | 90 | 0.3% |

[a]DMVCH (1 equiv), $Rh(acac)(CO)_2$ (0.1 mol %), $PPh_3$ (10 mol %), HCOOH (1.1 eq.), $Ac_2O$ (1.1 eq.), 2-MeTHF (1M), $H_2$ pressure, 90° C., 24 h;
[b]15 h, 90° C., no $H_2$ pressure, followed by addition of about 5 bar $H_2$ pressure; 90° C., 5 h.

In Examples 16a and 16b, the autoclave was pressurized with externally applied hydrogen gas to 4 bar and 10 bar, respectively, before heating to 90° C. Excellent conversion and selectivity to the desired aldehyde was achieved, with minimal hydrogenation side product produced (<5%). Under these conditions, the extent of oxidation of the phosphine-based ligand was less than 10%.

In Example 16c, the autoclave was sealed after nitrogen purge, but no hydrogen gas was introduced prior to heating. Pressure increased to 20 bar upon heating to 90° C., and remained constant with no observed conversion of the starting DMVCH; the observed pressure increase was due, in part, to thermal expansion, but also the generation of carbon monoxide. After 15 hours at 90° C., external hydrogen gas was applied until the system pressure increased to 25 bar, and then the sealed system was permitted to react for another 5 hours. After 5 hours, internal pressure had dropped to 10 bar, and 63% conversion was achieved with about 90% selectivity of the desired aldehyde and only 0.3% hydrogenation product. Under these conditions, the extent of oxidation of the phosphine-based ligand was less than 10%.

While the present invention was illustrated by the description of one or more embodiments thereof, and while embodiments have been described in considerable detail, they are not intended to restrict or in any way limit the scope of the appended claims to such detail. Additional advantages and modification will readily appear to those skilled in the art. The invention in its broader aspects is therefore not limited to the specific details, representative product and method, and illustrative examples shown and described. Accordingly, departures may be made from such details without departing from the scope of the general inventive concept embraced by the following claims.

What is claimed is:

1. A hydroformylation catalyst system useful for converting an olefin substrate to an aldehyde compound, the system comprising:

a hydroformylation catalyst complex comprising a Group 9 metal complexed with a phosphine-based ligand, wherein the Group 9 metal comprises rhodium;

a syngas surrogate comprising formic acid and an anhydride compound, which in the presence of the hydroformylation catalyst complex forms carbon monoxide, and optionally hydrogen, in situ; and optionally hydrogen gas, it being understood that, if the syngas surrogate does not form, in situ, hydrogen in the presence of the hydroformylation catalyst complex, the system comprises hydrogen gas;

wherein the phosphine-based ligand is selected from the group consisting of a monodentate phosphine ligand, a bidentate phosphine ligand, and combinations thereof; and wherein the bidentate phosphine ligand is selected from the group consisting of 1,2-bis(diphenylphosphino)ethane; 1,4-bis(diphenylphosphino)butane; 1,5-bis(diphenylphosphino)pentane; 1,6-bis(diphenylphosphino) hexane; 2,2'-bis(diphenylphosphino)-1,1'-binaphthyl, and combinations thereof.

2. The catalyst system according to claim 1, wherein the bidentate ligand is 1,2-bis(diphenylphosphino)ethane.

3. The catalyst system according to claim 1, wherein the rhodium is provided within a rhodium compound selected from the group consisting of $Rh(acac)(CO)_2$, $[Rh(COD)Cl]_2$, and $[(MeO)Rh(COD)]_2$.

4. The catalyst system according to claim 1, wherein the phosphine-based ligand is a monodentate phosphine ligand comprising at least one compound of the general formula (1):

$$PR^1R^2R^3 \qquad (1)$$

where $R^1$, $R^2$, and $R^3$ are each independently selected from a substituted or unsubstituted alkyl group having 1 to 20 carbon atoms;

a substituted or unsubstituted cycloalkyl group or cycloalkenyl group having 5 to 20 carbon atoms;

a substituted or unsubstituted aryl group having 6 to 36 carbon atoms;

a substituted or unsubstituted heteroalkyl group having 1 to 20 carbon atoms;

a substituted or unsubstituted heteroaryl group having 4 to 36 carbon atoms; or a substituted or unsubstituted hetero ring group having 4 to 36 carbon atoms, wherein the hetero alkyl group, the hetero aryl group, and the hetero ring group includes one or more atoms that are selected from the group consisting of N, O, and S;

wherein a substituent group is selected from the group consisting of nitro (—NO2), fluoride (—F), chloride (—Cl), bromide (—Br), and an alkyl group having 1 to 4 carbon atoms, when $R^1$, $R^2$, and $R^3$ are substituted by the substituent group.

5. The catalyst system according to claim 1, wherein the phosphine-based ligand is a monodentate phosphine ligand selected from the group consisting of triphenylphosphine, tri(m-tolyl)phosphine, diphenyl(p-tolyl)phosphine, tris(2,6-dimethoxyphenyl)phosphine, tris(4-methoxyphenyl)phosphine, trimesitylphosphine, tris-3,5-xylylphosphine, tricyclohexylphosphine, tribenzylphosphine, benzyl diphenylphosphine, diphenyl(2-methoxyphenyl)phosphine, and combinations thereof.

6. The catalyst system according to claim 1, wherein the anhydride compound comprises a compound having a general formula (3):

$$(R^7C{=}O){-}O{-}(O{=}CR^8) \qquad (3)$$

where $R^7$ and $R^8$ are independently selected from a substituted or unsubstituted alkyl or a substituted or unsubstituted aryl, where the substituent group may be a nitro (—NO2), fluoride (—F), chloride (—Cl), bromide (—Br), or an alkyl group having 1 to 4 carbon atoms.

7. The catalyst system according to claim 1, wherein a molar ratio of formic acid to anhydride is in a range from 1:1 to 4:1.

8. The catalyst system according to claim 1, further comprising hydrogen gas not derived from the syngas surrogate.

9. The catalyst system according to claim 1, wherein a molar ratio of rhodium to phosphine-based ligand is in a range of 1:1 to 1:500.

10. The catalyst system according to claim 1, wherein the rhodium is present in the catalyst system in an amount ranging from 0.0001 to 0.1 moles, based on 1 mole of the olefin substrate; and/or wherein the phosphine-based ligand is present in the catalyst system in an amount ranging from 0.001 to 10 moles, based on 1 mole of the olefin substrate.

11. A process for preparing the aldehyde compound using the catalyst system as claimed in in claim 1, the process comprising:

mixing the hydroformylation catalyst system of claim 1 with the olefin substrate to form a reaction mixture in a sealed reaction vessel; and reacting, in the reaction mixture, the olefin substrate with carbon monoxide produced from the syngas surrogate, and hydrogen gas, which is either derived from the syngas surrogate or not derived from the syngas surrogate, in the presence of the hydroformylation catalyst complex to form the aldehyde compound.

12. The process according to claim 11, further comprising:

isolating the aldehyde compound from the reaction mixture to provide an aldehyde product and a hydroformylation catalyst residue.

13. The process according to claim 12, wherein isolating the aldehyde compound comprises distilling the aldehyde compound from the reaction mixture to provide the aldehyde product and an undistilled fraction comprising the hydroformylation catalyst residue.

14. The process according to claim 12, wherein the reaction mixture is a first reaction mixture, said process further comprising recycling the hydroformylation catalyst residue by combining it with a second olefin substrate and the syngas surrogate comprising formic acid and the anhydride compound, and optionally hydrogen gas, to form a second reaction mixture; and reacting, in the second reaction mixture, the second olefin substrate with carbon monoxide produced from the syngas surrogate, and hydrogen gas, which is either derived from the syngas surrogate or not derived from the syngas surrogate, in the presence of the hydroformylation catalyst residue to form the aldehyde compound in the second reaction mixture.

15. The process according to claim 12, wherein the reaction mixture is a first reaction mixture, and wherein a portion of the phosphine-based ligand is converted to its corresponding phosphine oxide, the process further comprising quantifying the phosphine-based ligand and/or the corresponding phosphine oxide, and determining a molar ratio of the Group 9 metal to the phosphine-based ligand prior to and/or after isolating the aldehyde compound from the first and/or second reaction mixture.

16. The process according to claim 12, wherein the reaction mixture is a first reaction mixture, said process further comprising adding a sufficient quantity of the phosphine-based ligand to the hydroformylation catalyst system to adjust the molar ratio of Group 9 metal to phosphine-based ligand in a range from 1:5 to 1:500, prior to and/or after isolating the aldehyde compound from the first reaction mixture.

17. A process for preparing a fragrance product comprising the aldehyde compound obtained using the hydroformylation catalyst system as according to claim 1, the process comprising:

mixing the hydroformylation catalyst system according to claim 1 with the olefin substrate in a sealed reaction vessel;

reacting the olefin substrate with carbon monoxide produced from the syngas surrogate, and hydrogen gas, which is either derived from the syngas surrogate or not derived from the syngas surrogate, in the presence of the hydroformylation catalyst complex to form the aldehyde compound;

isolating the aldehyde compound; and optionally further reacting the aldehyde compound to form a derivative thereof and combining the isolated aldehyde compound or the derivative thereof with one or more fragrant compound(s) to obtain the fragrance product.

* * * * *